US00PP14444P39

(12) United States Plant Patent
Westhoff

(10) Patent No.: US PP14,444 P3
(45) Date of Patent: Jan. 6, 2004

(54) SUTERA PLANT NAMED 'WESBAWEI'

(50) Latin Name: *Sutera cordata*
Varietal Denomination: Wesbawei

(75) Inventor: Heinrich Westhoff, Fresenhorst 22-24, 46354 Südlohn/Oeding (DE)

(73) Assignees: Heinrich Westhoff (DE); Josef Westhoff (DE)

( * ) Notice: Subject to any disclaimer, the term of this patent is extended or adjusted under 35 U.S.C. 154(b) by 0 days.

(21) Appl. No.: 10/037,838

(22) Filed: Jan. 4, 2002

(65) Prior Publication Data

US 2003/0131388 P1 Jul. 10, 2003

(51) Int. Cl.[7] ..... A01H 5/00

(52) U.S. Cl. ..... Plt./263
(58) Field of Search ..... Plt./263

(56) References Cited

U.S. PATENT DOCUMENTS

| | | | | | |
|---|---|---|---|---|---|
| PP10,966 | P | * | 6/1999 | Rother | Plt./263 |
| PP12,026 | P2 | * | 7/2001 | Theobald | Plt./263 |
| PP12,682 | P2 | * | 6/2002 | Polman | Plt./263 |
| PP12,689 | P2 | * | 6/2002 | Churchus | Plt./263 |

* cited by examiner

*Primary Examiner*—Bruce R. Campell
*Assistant Examiner*—Susan B. McCormick
(74) *Attorney, Agent, or Firm*—Webb Ziesenheim Logsdon Orkin & Hanson P.C.

(57) ABSTRACT

A new and distinct Sutera plant with large white colored flowers and vigorous growth with long weeping branches.

1 Drawing Sheet

Botanical classification: *Sutera cordata.*
Varietal denomination: 'Wesbawei'.

BACKGROUND OF THE INVENTION

The present invention comprises a new and distinct cultivar of Sutera plant known by the varietal name 'Wesbawei'. The new variety was discovered in 2000 in a selected breeding program in Südlohn, Germany. The new variety is a selection from the cross of proprietary unpatented breeding plants. The growth character of the new variety is similar to its parents but with bigger flowers. The new variety was first asexually reproduced in December 2000 by cuttings in Südlohn, Germany. The new variety has been trial and field tested at Südlohn and has been found to retain its distinctive characteristics and remain true to type through successive propagations.

The following traits in combination distinguish 'Wesbawei' as a new and distinct cultivar:

1. Large buds and flowers.
2. Strong, wiry branches.
3. Large leaves.
4. Broad, rhombic leaves.
5. Crenate to dentate leaf margin.
6. Needle-shaped sepals.
7. Long peduncles.

The new variety has similar colored flowers to the unpatented varieties 'Snowflake' and 'Cabane'. However, 'Wesbawei' has longer, thicker, and more weeping branches and longer peduncles compared to 'Snowflake' and 'Cabane'. The leaves of 'Wesbawei' are about twice the overall size of those of 'Snowflake' and 'Cabane' with broader dentation on the margins. The flowers of 'Wesbawei' are also larger than the compared varieties in overall size, throat diameter, tube length, and petal length.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Südlohn, Germany. Plants grown for the description were 20 weeks old, grown in a greenhouse at 20–25° C. daytime temperature and at 16–18° C. night temperature with light levels of 3,000–50,000 lux. The color readings were taken on a plant outdoors and in a greenhouse under natural light. Color references are primarily to The R.H.S. Colour Chart of The Royal Horticultural Society of London.

PLANT

Classification:
*Botanical.*—*Sutera cordata.*
*Commercial.*—Bacopa.
Form: Hanging with long weeping branches.
Height: 10–14 cm from soil to top of flowers; 1.15 m wide.
Growth: Vigorous.
Roots:
*Habit.*—Fine, well-branched.
*Time to initiate roots.*—About 10 days at 20° C.
*Time to develop roots.*—About 28 days at 20° C.
Main stem: 1.1 m long; 2.35 mm diameter; Green Group 143A.
Lateral branches:
*Form.*—Hanging, weeping.
*Color.*—Green Group 143A.
*Texture.*—Pubescent (very short, dense, white hairs).
*Diameter.*—1.4 mm.
*Length.*—28–80 cm.

*Internode length.*—2.8 cm.
*Quantity.*—2 per node at half proximal branch.

Foliage:
*Arrangement.*—Opposite.
*Number of leaves per branch.*—2 per node.
*Size of leaf.*—Length: 2.3 cm. Width: 2.4 cm.
*Shape of leaf.*—Broad rhombic.
*Shape of apex.*—Acute.
*Shape of base.*—Truncate.
*Texture.*—Young leaves: Minimal, very short pubescence. Mature leaves: Almost absent, very short pubescence.
*Aspect.*—Slightly cupped.
*Margin type.*—Crenate to dentate.
*Color.*—Young leaves: Upper surface: Yellow-Green Group 146A. Lower surface: Yellow-Green Group 146B. Mature leaves: Upper surface: Yellow-Green Group 147A. Lower surface: Yellow-Green Group 147B.
*Petioles.*—Length: 7.5 mm. Diameter: 1 mm. Color: Yellow-Green Group 146A.
*Veins.*—Color: Upper surface: Yellow-Green Group 147A. Lower surface: Yellow-Green Group 146B.

FLOWER

Natural flowering season: Spring through autumn until frost; tolerates temperatures of about 4–30° C.
Flower type and habit: Single, salverform; long lasting; persistent.
Average number of blooms per stem: 5–7.
Fragrance: None.
Flower size:
*Diameter.*—1.9 cm.
*Length.*—1.45 cm.
*Tube length.*—1.3 cm.
*Tube diameter.*—Distal end: 0.45 cm. Proximal end: 0.17 cm.

Corolla:
*Petal length from throat.*—8 mm.
*Petal width.*—8.1 mm.
*Petal quantity.*—5, fused.
*Petal apex shape.*—Obtuse.
*Texture.*—Smooth.

Color:
*Petals.*—When opening: Upper surface: Lighter than White Group 155D. Lower surface: Lighter than White Group 155D. Fully opened: Upper surface: Lighter than White Group 155D, changing to White Group 155D over time. Lower surface: Lighter than White Group 155D.
*Flower throat inside surface.*—Yellow-Orange Group 21A; not veined.
*Flower tube.*—Outside: Tip: White Group 155D. Middle: Yellow-Orange Group 20B. Base: Yellow-Green Group 145C. Veins: Not veined.

Peduncle:
*Length.*—1.2 cm.
*Diameter.*—0.5 mm.
*Color.*—Yellow-Green Group 146A.
*Orientation.*—Acute angle.
*Strength.*—Flexible.

Bud:
*Shape.*—Oblanceolate.
*Length.*—1–1.2 cm.
*Diameter.*—2.5 mm.
*Color.*—Green-White 157A.

Calyx:
*Arrangement.*—Whorled.
*Length.*—1 cm.
*Diameter.*—2.5–3 mm.
*Sepals.*—Shape: Needle; tip is acute. Width: 0.5–1.7 mm. Margin: Entire. Texture: Leathery; pubescent. Color: Upper surface: Green Group 137A. Lower surface: Green Group 137A.

REPRODUCTIVE ORGANS

Stamens:
*Number.*—4; on two plains (2 high, 2 low); fused with petals.
*Filament length.*—4.1 mm and 3.1 mm.
*Anthers.*—Shape: Flat, reniform. Length: 0.7 mm. Width: 1.7 mm. Color: Yellow-Orange Group 21A.
*Pollen.*—Color: Yellow-Orange Group 21A. Amount: Moderate to abundant.

Pistil:
*Length.*—1.3 cm.
*Style.*—Length: 0.9 cm. Color: Yellow-Green Group 144A.
*Stigma.*—Shape: Ovate; narrow. Color: Yellow-Green Group 144B. Ovary color: Yellow-Green Group 146A.

Seeds: Generally none.
Disease/pest resistance: No unusual susceptibility to diseases or pests has been noted to date.

I claim:

1. A new and distinct variety of Sutera plant substantially as shown and described.

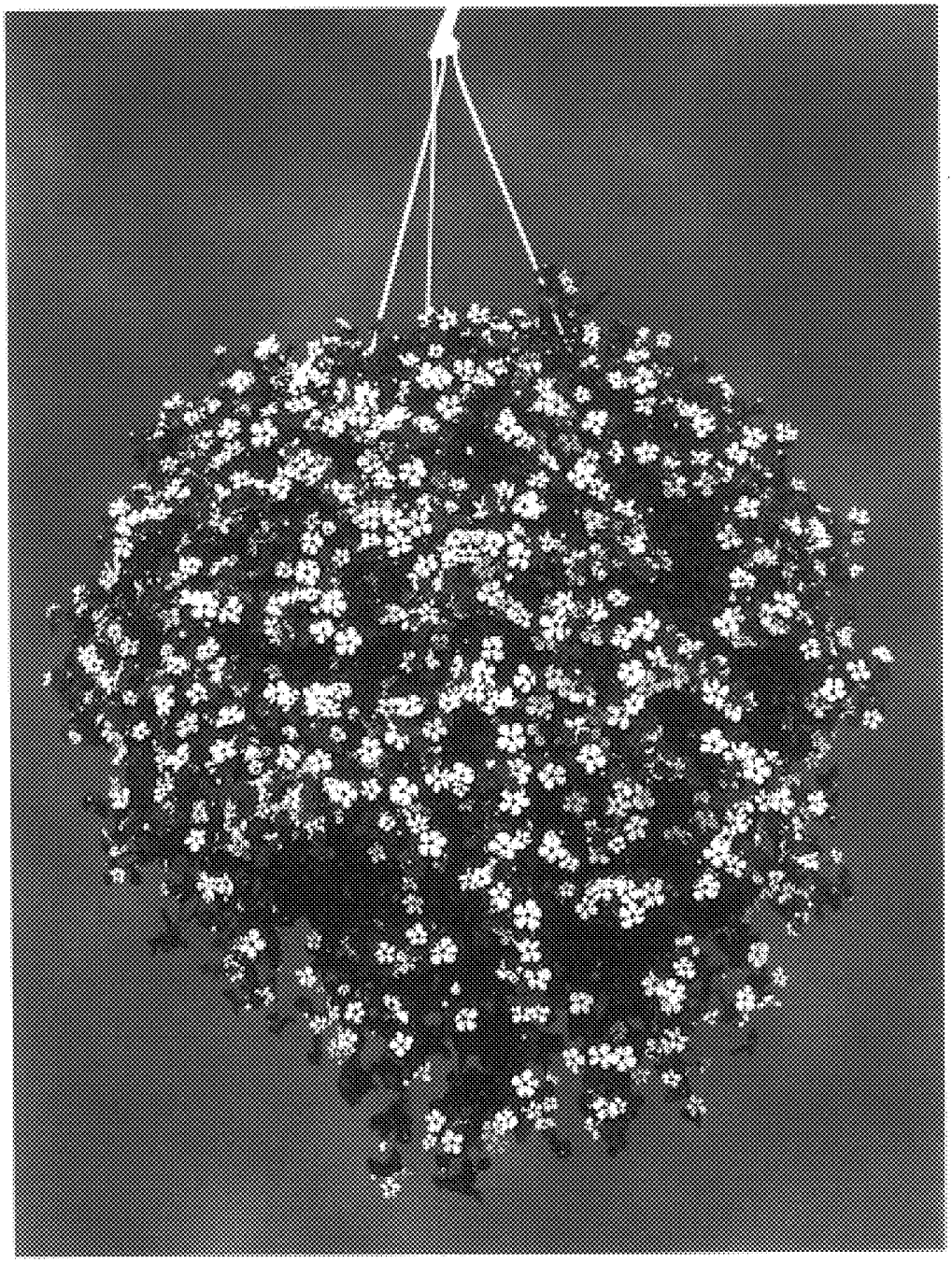

* * * * *